United States Patent [19]

Lopez et al.

[11] 4,331,021
[45] May 25, 1982

[54] CONTRAST RESOLUTION TISSUE EQUIVALENT ULTRASOUND TEST OBJECT

[75] Inventors: Hector Lopez, Kensington; Stephen W. Smith, Rockville, both of Md.

[73] Assignee: The United States of America as represented by the Secretary of the Department of Health and Human Services, Washington, D.C.

[21] Appl. No.: 186,381

[22] Filed: Sep. 11, 1980

[51] Int. Cl.³ .......................................... G01N 29/00
[52] U.S. Cl. .................................................. 73/1 DV
[58] Field of Search .............. 73/1 R, 1 DV, 570, 584

[56] References Cited

U.S. PATENT DOCUMENTS 3,933,026  1/1976  Ham et al. ........................... 73/1 R
4,116,040  9/1978  Schoknecht ......................... 73/1 R
4,286,455  9/1981  Ophir et al. ....................... 73/1 DV

OTHER PUBLICATIONS

Madsen et al., Tissue Mimicking Materials for Ultrasound Phantoms, Med. Phys. 5(5) Sep./Oct. 1978, pp. 391-394.
Wisconson Ultrasound Tissue Phantoms, published by Radiation Measurments Inc., Box 44, Middleton, Wisc. 53562, 2 pages.
Carson, P. L., What a Hospital Physicist Needs in a Transducer Characterization Standard, etc. IEEE, Transact on Sonics and Ultrasonics, vol. S.U. 26 No. 1, Jan. 1979.

*Primary Examiner*—S. Clement Swisher
*Attorney, Agent, or Firm*—Holman & Stern

[57] ABSTRACT

A contrast resolution tissue-equivalent ultrasound test phantom comprises a block of material having ultrasonic propagation characteristics similar to that of human or animal tissue. A plurality of contrast objects are embedded in the block, each having a different reflectivity. The contrast objects have at least one dimension wherein the size of the object in cross-section decreases so that periodic ultrasonic scans of all of the objects simultaneously produce successive displays of plural cross-sectional patterns, the pattern in each display having the same size but different contrasts whereas the pattern size changes for successive displays.

8 Claims, 3 Drawing Figures

CONTRAST RESOLUTION TISSUE EQUIVALENT ULTRASOUND TEST OBJECT

TECHNICAL FIELD

The present invention relates to a calibration phantom or test object for simulating animal or human cell tissue which can calibrate, or test diagnostic ultrasound scanners.

BACKGROUND OF THE INVENTION

Ultrasonics has been used in the prior art for purposes of medical diagnosis. Specifically, ultrasonic pulses are transmitted into the body and tissue boundaries produce reflection of the pulses. The transit time of a transmitted and reflected pulse can be measured to provide a determination of the depth of such a boundary.

There is a considerable overlap in the diagnostic uses of ultrasound and computed tomography. Each modality produces cross-sectional images of soft tissue with high spatial resolution and excellent contrast sensitivity or tissue differentiation. However, the imaging mechanisms of the two modalities are entirely different. In computed tomography, an image is mathematically reconstructed utilizing a back-projection algorithm to produce a two-dimensional mapping of X-ray attenuation coefficient. The contrast sensitivity of computed tomography displays local changes in X-ray absorption coefficient of 0.5% of the absorption coefficient of water anywhere in the tomographic image. On the other hand, for diagnostic ultrasound, reflected or scattered mechanical energy is utilized to form images directly. Reflections occur due to the changes in acoustic impedance at every tissue interface. Generally speaking, acoustic impedance of material is the product of its density and the speed of the acoustic waves in the material. In soft tissue imaging, the impedance varies over a range of 60 dB. Even the small changes in the impedance parameter which are associated with soft tissue interfaces (as low as 1 part in a million) are easily detected, resulting in excellent contrast sensitivity.

For each of the computed tomography and ultrasound modalities, a feature of prime importance is the ability to detect lesions of varying size and contrast from the background tissue. For both modalities, the capability of displaying low contrast lesions in a tissue background is limited by two intrinsic imaging parameters, namely: the spartial resolution, and the image noise. These two aspects of image quality have been extensively analyzed and are readily predictable for computed tomography; however, there is very little knowledge concerning image quality characteristics for diagnostic ultrasound devices.

For both the computed tomography and diagnostic ultrasound modality, the limiting three-dimensional spatial resolution for high contrast objects can be described by either the point spread function (PSF) or its Fourier transform, the modulation transfer function (MTF). The analogous two-dimensional spatial resolution within a tomographic image of a given thickness is described by the line spread function (LSF) and its modulation transfer function. The spatial resolution for computed tomography scanners varies to a limited extent over the field of view. The spatial resolution of pulse echo diagnostic ultrasound differs in the axial versus the lateral image dimensions. In the axial dimension, the resolution is determined by the pulse length of the propagating ultrasound pulse. In the perpendicular lateral dimension, due to the wave nature of ultrasound radiation, the spatial resolution is diffraction-limited, depending on the ultrasound wavelength and the f number of a focused transducer. Therefore, for fixed focus ultrasound imaging systems, lateral resolution varies throughout the image field of view. In view of the variation of the spatial resolution with position for both computed tomography and ultrasound, measurements of LSF or MTF should be made at many points in the image and the results averaged to provide a two-dimensional description of spatial resolution.

Spatial resolution or LSF for both diagnostic ultrasound and computed tomography scanners has traditionally been measured by scanning high contrast wires or rods in a water medium. Spatial resolution for abdominal computed tomography systems is on the order of 1 mm square. For diagnostic ultrasound abdominal scanners, axial resolution is optimally about 2 mm and lateral resolution varies from 2 mm at the transducer focus to 1 cm near the transducer and in the far field. In the case of diagnostic ultrasound, high contrast spatial resolution can also be measured by imaging wires or rods suspended in an attenuating tissue equivalent material. Such tissue equivalent resolution phantoms are now commercially available, such as the Model 412 Tissue Phantom manufactured and sold by Radiation Measurements, Inc. of Middleton, Wis., and such as the device illustrated and described in U.S. Pat. No. 4,116,040. Measurements indicate that spatial resolution deteriorates significantly in a tissue medium, primarily due to the frequency-dependent attenuation of tissue and phase-aberration effects of intervening tissue.

The ability of a medical imaging modality to detect a low contrast lesion from a tissue background is limited by the noise in the image. For both computed tomography and diagnostic ultrasound, the noise can be described by the standard deviation of the fluctuation in image intensity from the mean background of an image of a standard uniform test object. Each of the described modalities is subject to electronic noise. Computed tomography also suffers from noise generated due to the algorithm in the mathematical image reconstruction; however, the main noise sources for the two imaging modalities are distinctly different. In computed tomography, as in all radiographic imaging, the primary noise source is quantum mottle, or fluctuations in image background directly related to the photon statistics of image formation. The greater the radiation dose, the less the image noise. In diagnostic ultrasound, the primary noise source is not a function of exposure statistics, but rather is due to coherent speckle, a phenomenon common to all coherent imaging (for example, laser optics). In scanning an abdominal organ, large numbers of scatterers are present in the tissue. Interference effect in the echoes from the multiple scatterers cause severe fluctuations in the image background level which obscure important diagnostic signals.

Due to the restrictions of spatial resolution and image noise for diagnostic ultrasound and computed tomography, low contrast detectability of these modalities is limited. The low contrast performance of these systems can be measured directly using suitable phantoms in the form of objects of varying size and contrast embedded in a tissue-equivalent medium. Several "contrast detail" phantoms have been developed and evaluated for computed tomography applications. An extensive investigation of computed tomography contrast-detail-dose interdependency is described in an article by Cohen, et al., entitled "The Use of a Contrast-Detail-Dose Evaluation of Image Quality in a Computed Tomographic Scanner" appearing in the Journal of Computer Assisted Tomography, Volume 3, pages 189-195, 1979. This paper describes the utilization of the partial volume effect in radiography whereby a phantom was developed containing cylindrical objects varying in contrast from 0.2% to 3% over a range of diameters from 16 mm down to 1 mm. Utilizing this phantom, the threshold of perceptibility of patterns of disks was measured utilizing multiple observers for several computed tomography scanners and dose values. The results for computed tomography indicated the contrast-detail-dose relationship could be divided into (1) a high contrast region (10%-100%) wherein the detection capability was strongly dependent upon the system spatial resolution (MTF) and weakly dependent upon noise (dose) and contrast; (2) a transition contrast region (1%-10%) wherein lesion detectability was dependent upon contrast, noise (dose) and MTF; and (3) a low contrast region (0.1%-1%) wherein the detection was strongly dependent upon image noise, that is, dose. Therefore, for low contrast lesions, image noise becomes the limiting characteristic for detection in computed tomography.

In the field of diagnostic ultrasound, only rudimentary efforts have been made to study the detection capability of low contrast targets. Tissue-equivalent phantoms containing simulated cysts are commercially available and another phantom is marketed containing cylindrical objects whose reflectivity varies from background tissue by 1 dB and 10 dB. These phantoms utilize tissue-equivalent materials of water-based gelatins. Oil-based gels have also been utilized to construct an anthropomorphic ultrasound phantom. However, there has been no attempt to include low contrast objects suitable for quantitative measurements of low contrast detectability of an ultrasound scanner. In each of the prior art phantoms, the variation in contrast or reflectivity is obtained by varying the concentration and particle size of scatterers in the gel matrix of the artificial tissue. For the oil-based gel, polyvinylchloride particle sizes ranging from 100 microns to 260 microns, with concentrations of 0.3 particles per cubic millimeter to 2.0 particles per cubic millimeter demonstrated a reflectivity range from $-25$ dB to $+5$ dB relative to the reflectivity of liver.

Thus, where prior art test objects and phantoms enable the evaluation of high contrast resolution in water or tissue-equivalent media, the true efficacy of ultrasound scanners depends upon the ability of such scanners to detect low contrast lesions in tissue. Prior art phantoms simply do not have this low contrast measurement capability. Clearly, then, there is a need for a tissue-equivalent ultrasound phantom capable of permitting measurement of the relationship between threshold detection of lesions of varying size versus contrast (reflectivity).

SUMMARY OF THE INVENTION

It is therefore a primary object of the present invention to provide a contrast resolution tissue-equivalent ultrasound phantom for diagnostic ultrasound scanners which will enable the measurement of the relationship between threshold detection of lesions of varying size versus image contrast or reflectivity in a tissue-equivalent medium.

It is another object of the present invention to provide a contrast resolution tissue-equivalent ultrasound phantom which is compact, inexpensive to manufacture and easily utilized by clincal personnel.

In accordance with the present invention, a contrast resolution tissue-equivalent test phantom is provided in the form of a block of tissue-equivalent material. The material may be a water-based or oil-based gelatin which contains suspended acoustic scattering particles having acoustic scattering properties similar to living tissue. A plurality of cavities are defined in the block and are filled with tissue-equivalent material having respectively different acoustic scattering properties. The cavities are configured to present similar sized cross-sections to the ultrasonic scanner for each cross-sectional scan. The dimensions of the cavities vary transversely to the scan plane so that successively smaller (or larger) cross-sectional images are presented with each succeeding scan.

In the preferred embodiment, the cavities are conical in shape. The reflectivity of the material in the respective cavities varies in steps over a 30–60 dB range in the preferred embodiment. Cross-sectional scans, perpendicular to the lengths of the conical cavities, at various positions along the lengths of the cavities result in images of disks of a constant diameter but varying contrasts. The scans permit observation of the resolution capability of the ultrasonic scanner for the varying contrasts (reflectivities) of the cavities for different size cross-sections.

BRIEF DESCRIPTION OF THE DRAWINGS

The accompanying drawings will be more clearly understood when taken in conjunction with the following description, wherein.

DESCRIPTION OF THE PREFERRED EMBODIMENTS

Figure 1:
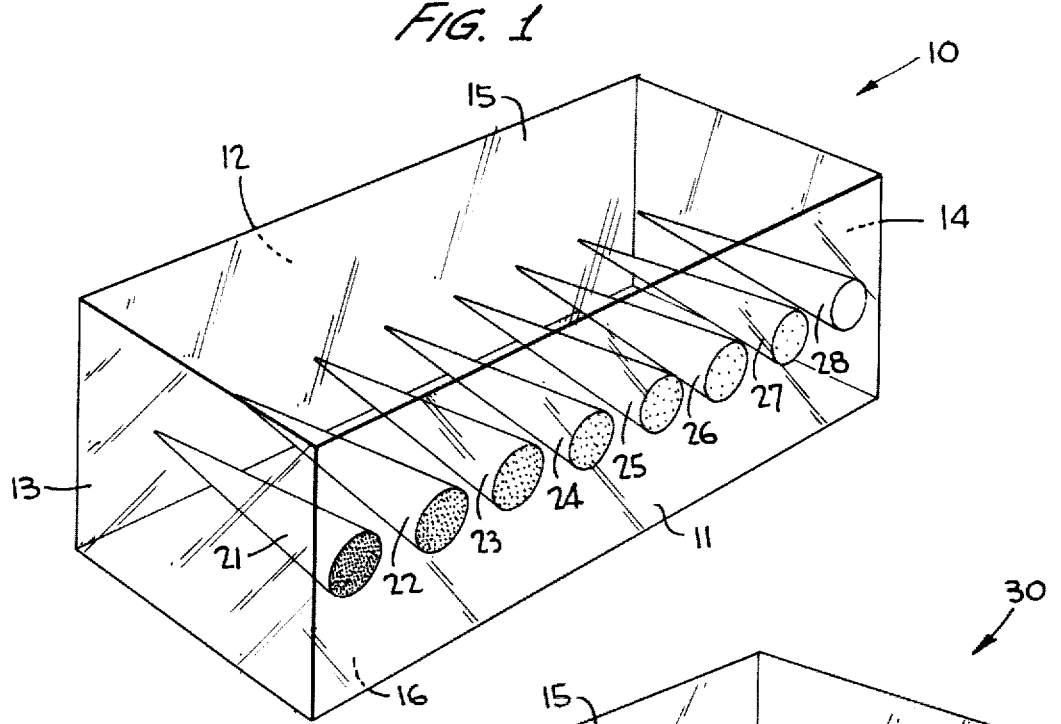
FIG. 1 is a view in perspective of a test phantom constructed in accordance with the principles of the present invention.

Referring specifically to FIG. 1 of the accompanying drawings, a block 10 of tissue-equivalent material is shown as being fully transparent to facilitate understanding; it is understood however that the tissue material need not be, and in most instances will not be, transparent. Further, the block 10 is shown as a right angle parallellepiped having front surface 11, rear surface 12, side surfaces 13 and 14, top surface 15 and bottom surface 16. This configuration is for convenience in fabrication but is by no means limiting on the scope of the invention. The tissue-equivalent material is preferably a gel and is selected to have a density and an ultrasound propagation velocity which simulates those of human or animal tissue. In addition, acoustic scatterers are interspersed homogeneously throughout the gel to further simulate desired tissue. For example, the gel could be a water-based gel such as agar in which particles of graphite, polyvinylchloride, glass micro-balloons, or the like are interspersed homogeneously as scatterers. Likewise, an oil-based gel can be employed with similar scatterer particles. Oil-based gels are well known and a variety of such gels can be employed for this application. A particularly suitable oil-based gel can be made from Kraton, a styrene-butadiene resin sold by Shell Oil Company, mixed with mineral oil absorbed in butadiene chains; the mixture is gelled by heating to 130° C. for 1-half hour. This gel is described in greater detail in the final report "Development of an Ultrasound Phantom" dated Jan. 25, 1979 submitted under U.S. FDA Contract No. 233-77-6017. Such material closely simulates liver parenchymal tissue in acoustic imaging.

A series of conical contrast objects 21–28, inclusive, are embedded in block 10 with their axes oriented mutually parallel and coplanar in a plane parallel to top surface 15 and bottom surface 16 of block 10. The cones are substantially identical in size, decreasing in diameter in the direction from front surface 11 to rear surface 12 of block 10. Contrast objects 21–28 are formed by inserting correspondingly shaped molds in block 10 before the gel is formed and then removing the molds after gelling to provide conical cavities. The cavities are then filled with tissue-equivalent material which is allowed to gel. Contrast objects 21–28 are preferably made of the same gel material as block 10 but each has a different acoustic scattering property so that net effect is that the contrast objects are each of different tissue-equivalent material and of different tissue-equivalent material from block 10. Variation of acoustic scattering properties between contrast objects 21–28 can be achieved by changing the density of scatterer particles in each contrast object, using different size scatterer particles in each object, etc. Typically, the acoustic scattering in contrast objects 21–28 is varied to achieve a reflectivity variation on the order of 30 dB. One contrast object, for example, object 21, has substantially cyst-like reflectivity properties, so that objects 22–28 preferably have reflectivities which vary in 3.75 dB steps to provide an overall range of 26.25 dB, this being typical of the dynamic range of soft tissue echoes. If reflectivity variation is achieved by means of changing scatterer particle size, spherical particles may be utilized having diameters over a range of ten to four hundred microns.

In an embodiment which has been constructed and found to operate satisfactorily, contrast objects 21–28 are located at a depth of approximately 7.5 cm below top surface 15 in order to simulate the depth of typical abdominal organs. The angle subtended by the conical contrast objects is chosen so that the variation in diameter of the cone across the beam width of an ultrasonic transducer is small. For example, for a transducer beam width of 13 mm, the diameter of the cross-section of the cone should vary by only 1.3 mm over a 13 mm length. Therefore, the cone angle would be approximately 5.6°. In order to obtain image disk diameters from 0 to 2 cm, a total cone length of 20 cm would be required. Consistent with these dimensions, the length of top surface 15 and bottom surface 16 would typically be 25 cm; the height of the block is typically 12 cm. The depth of the block depends upon the desired length of conical contrast objects 21–28 but in a typical embodiment, is 12 cm, the cones for such embodiment being 10 cm long. The bases of the cones are 2 cm in diameter and are spaced apart by 1 cm. These dimensions are, of course, by way of example only, and are not deemed limiting on the scope of the present invention.

Figure 3:
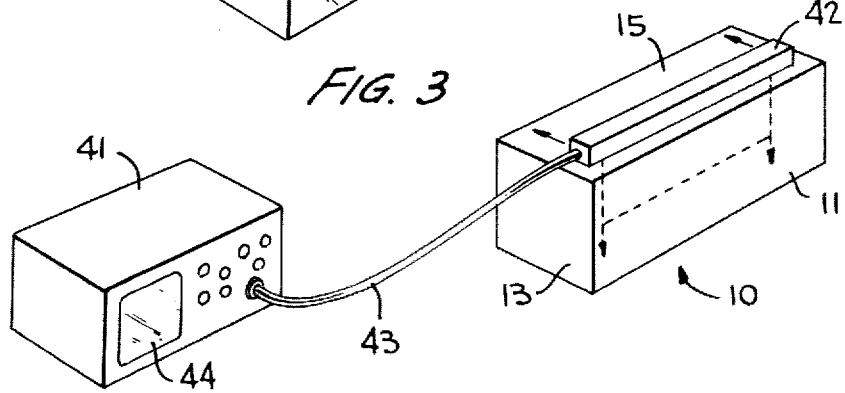
FIG. 3 is a view in perspective illustrating a test phantom according to the present invention utilized in conjunction with an ultrasonic scanner.

The phantom illustrated in FIG. 1 is shown in use in the schematic diagram of FIG. 3. An ultrasound scanner is shown to include a console 31 and transducer 32 interconnected by cable 33. A typical scanner which serves the purpose described in relation to the present invention is the Model 2130 manufactured by ADR Ultrasound of Tempe, Ariz. Transducer 32 transmits an ultrasonic pulse beam in a plane defined by the length dimension of the transducer. Reflections of the beam energy are received by the transducer and transmitted back to the console 31 via cable 33 and displayed on console oscilloscope 34. As illustrated in FIG. 3, transducer 32 is oriented in the width dimension of block 10 so that the beam strikes the same size diameter portion of each contrast target 21–28. This cross-sectional scan of each contrast target results in an image on oscilloscope 34 of eight generally circular disks having varying reflectivities depending upon the scattering properties of each contrast object. A series of scans are made at different locations along top surface 15 of block 10 as indicated by the arrows in FIG. 3. Thus, successive scans are made perpendicular to the length of the contrast objects at various positions along the cone length. The diameter of the eight image disks in any scan will be the same, but will change from scan to scan as the transducer is moved. The contrast or reflectivity of the eight disks in any given scan varies in accordance with the reflectivity or scattering properties of the contrast objects. If desired, the diameter of threshold detection for lesions of varying contrasts can be utilized to construct curves of contrast versus diameter. The various scans permit measurement of the relationship between threshold detection of lesions varying in size versus image contrast or reflectivity in the tissue-equivalent medium.

Figure 2:
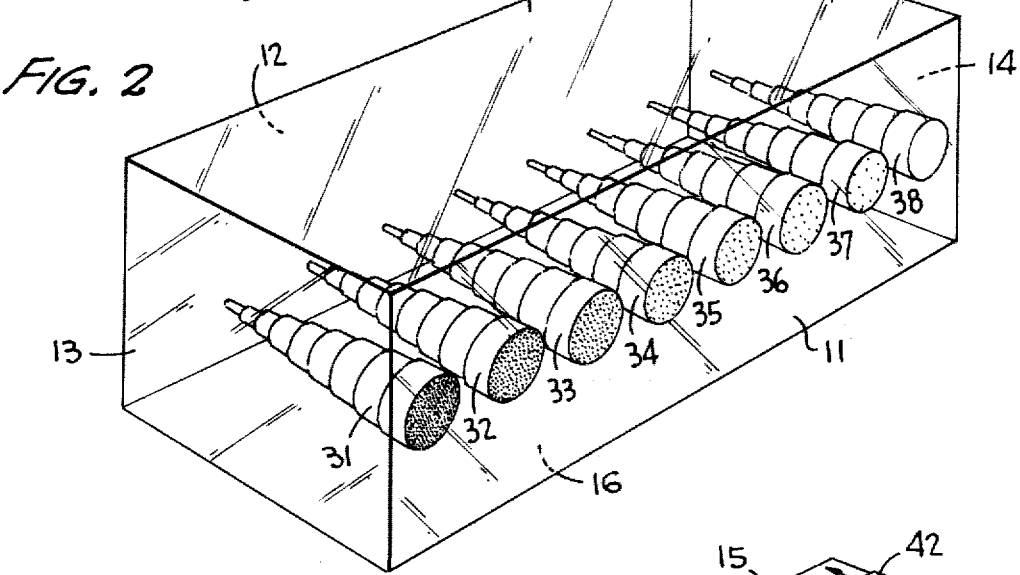
FIG. 2 is a view in perspective of an alternative embodiment of the test phantom constructed in accordance with the principles of the present invention.

Another embodiment of the test phantom is illustrated in FIG. 2 wherein like elements are designated by like reference numerals. Specifically, a block 30 of tissue-equivalent material, identical to block 10 of FIG. 1, includes contrast objects 31–38 which, instead of being conical in shape, are configured as plural cylinders of decreasing diameter. Contrast objects 31–38 are constructed in the same manner described above in relation to contrast objects 21–28 and have acoustic scattering properties which are made to vary in the same manner as that described in relation to FIG. 1. Successive scans of block 30 are made at corresponding cylinder diameters. The test phantom of FIG. 2 is otherwise identical to that described above in relation to FIG. 1.

It should be noted that the specific location and number of contrast objects described above is not limiting on the scope of the present invention. For example, instead of eight contrast objects for producing eight simultaneous disk images, as few as two contrast objects, each having a different reflectivity, may be employed to provide a meaningful comparison of contrast for successive scans at different object diameters. Likewise, the maximum number of test targets is limited only by the practicalities of size and meaningful test results for a given application. The shape of the contrast object need not be conical or discretely stepped cylinders as described, but instead may take any shape in which the cross-section in the plane of the ultrasound scanning beam changes to simulate lesions of different size with each scan. For example, a pyramid or any other generally converging shape may be employed. Likewise, the cone or pyramid may be truncated, if desired. Of further note is the fact that the contrast objects, while preferably disposed in a plane parallel to the top surface of the block, may be positioned at different heights in the block for certain applications of the phantom. In any variation from the specific embodiments described herein, the important point to consider is that the contrast objects must provide varying contrasts and changing dimensions so that each individual scan yields a plurality of images of different contrasts whereas successive scans yield images of different size.

The present invention is not to be limited to the exact details of construction as shown and described herein, for obvious modifications can be made by a person skilled in the art.

The embodiments in which an exclusive property or privilege is claimed are as follows:

1. A tissue-equivalent phantom for diagnostic ultrasound scanners, comprising:
   a block of material having a tissue-equivalent acoustic velocity characteristic;
   a plurality of contrast objects embedded into the block, each contrast object being made from a tissue-equivalent material and having a different reflectivity from the reflectivity from all others of said contrast objects, said contrast objects having at least one dimension along which its cross-sectional size varies.

2. The test phantom according to claim 1 wherein said block is made from a water-based gel, wherein said contrast objects are made from a water-based gel, and wherein the reflectivities of said contrast objects are determined by acoustic scatterer particles homogeneously distributed in said contrast objects.

3. The test phantom according to claim 1 wherein said block is made from an oil-based gel, wherein said contrast objects are made from an oil-based gel, and wherein the reflectivities of said contrast objects are determined by acoustic scatterer particles homogeneously distributed in said contrast objects.

4. The test phantom according to claim 2 or 3 wherein, in order to obtain different reflectivities for said contrast objects, said particles are distributed in different densities in said contrast objects.

5. The test phantom according to claim 2 or 3 wherein, in order to obtain different reflectivities, said particles differ in size in different contrast objects, respectively.

6. The test object according to claim 1, 2 or 3 wherein said contrast objects are in the shape of cones of substantially the same size positioned adjacent to one another, each cone having a central longitudinal axis which is parallel to and substantially co-extensive with the central longitudinal axis of the other cones.

7. The test phantom according to claim 1, 2 or 3 wherein said contrast objects are each in the shape of plural cylinders of different size disposed end to end along a central axis, the central axes of all contrast objects being parallel to and co-extensive with one another.

8. The method of determining contrast and resolution with respect to object size of diagnostic ultrasound scanners, said method comprising the steps of:
   scanning, with an ultrasonic beam, a plurality of side-by-side contrast objects of different reflectivities embedded in a tissue-equivalent material, said scanning taking place simultaneously through similarly sized and shaped cross-sections in each contrast object;
   repeating said scanning step at different portions of said contrast objects having different sizes; and
   displaying the results of each scan in the form of the cross-sectional pattern of ultrasonic reflections received from each contrast object.

* * * * *